(12) United States Patent
Ishii et al.

(10) Patent No.: US 6,880,401 B2
(45) Date of Patent: Apr. 19, 2005

(54) FATIGUE TEST DEVICE AND METHOD FOR TESTING THE THIN PLATE

(75) Inventors: Kazuo Ishii, Wako (JP); Yoshihiro Odagiri, Wako (JP); Hitoshi Ishii, Hamamatsu (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/464,825

(22) Filed: Jun. 19, 2003

(65) Prior Publication Data

US 2004/0020293 A1 Feb. 5, 2004

(30) Foreign Application Priority Data

Jun. 19, 2002 (JP) ........................................ 2002-178312

(51) Int. Cl.[7] .............................................. G01M 7/00
(52) U.S. Cl. ............................ 73/577; 73/812; 73/856
(58) Field of Search ......................... 73/577, 578, 663, 73/812, 856

(56) References Cited

U.S. PATENT DOCUMENTS

| | | | | |
|---|---|---|---|---|
| 2,500,764 A | * | 3/1950 | MacGeorge | 73/578 |
| 2,541,080 A | * | 2/1951 | Lyon | 198/816 |
| 2,573,168 A | * | 10/1951 | Mason et al. | 74/1 SS |
| 2,936,612 A | * | 5/1960 | Mason | 73/577 |
| 3,023,610 A | * | 3/1962 | Prochazka | 73/578 |
| 3,131,515 A | * | 5/1964 | Mason | 451/28 |
| 3,187,566 A | * | 6/1965 | Coombs | 73/663 |
| 3,600,934 A | * | 8/1971 | Hendrix et al. | 73/570 |
| 4,122,797 A | * | 10/1978 | Kawamura et al. | 116/137 A |
| 6,698,288 B1 | * | 3/2004 | Shirzad et al. | 73/577 |

FOREIGN PATENT DOCUMENTS

JP       08-054331       2/1996

OTHER PUBLICATIONS

JIS Handbook, "Ferrous Materials & Metallurgy I," Terms, 2002, Japanese Standards Association.

* cited by examiner

Primary Examiner—Hezron Williams
Assistant Examiner—John C Hanley
(74) Attorney, Agent, or Firm—Arent Fox, PLLC

(57) ABSTRACT

A fatigue test device for thin plates can reliably perform tests. The fatigue test device has a rod having ends in a longitudinal direction thereof; a vibration source for excitating a longitudinal end of the rod in the longitudinal direction thereof so as to form a standing wave having node portions and antinode portions formed therebetween and a mounting means for mounting a test piece having a longitudinal direction at one of the antinode portions, the test piece being positioned such that the longitudinal direction thereof is perpendicular to the longitudinal direction of the rod.

7 Claims, 6 Drawing Sheets cross-sectional shape
of holding portion of cylinder cross-sectional shape
of test piece

FATIGUE TEST DEVICE AND METHOD FOR TESTING THE THIN PLATE

BACKGROUND OF THE INVENTION

1. Field of the Invention

The present invention relates to a fatigue testing device for thin plates and to a fatigue test method for the same, and specifically relates to a fatigue test technique in which the fatigue test can be reliably performed.

2. Description of the Related Art

Thin plates which form metal diaphragms and metal gaskets must have sufficient elasticity and flexibility against pressure and temperature, and must maintain necessary seal against pressure in order to prevent leakage at joined surfaces. Therefore, excellent fatigue characteristics are required in these thin plates. It is important to perform fatigue tests for the thin plates forming metal diaphragms to verify fatigue characteristics when metal diaphragms are produced.

As examples of fatigue tests for thin plates proposed heretofore, there are the "Plane bending fatigue test method for metallic plate" according to JIS Z 2275 and "Fatigue test method and fatigue test device using resonance" described in Japanese Patent Unexamined (KOKAI) Publication No. 8-54331, etc.

In the above-mentioned plane bending fatigue test method for metallic plates, bending moment is set to perform the fatigue test. In this method, the bending moment must be extremely small when the thickness of a test piece is extremely thin, for example 0.5 mm or less, or else the fatigue test cannot be performed. In the test, both ends of the test piece are bent by providing moment with a mechanical structure, so that the cycle frequency is very low, for example, about 50 Hz. Therefore, the fatigue test requires 20 days or more in a case of an ultra-high cycle, for example, $10^8$ or more, and the fatigue test cannot be performed quickly.

In contrast, "Fatigue test method and fatigue test device using resonance" described in Japanese Patent Unexamined (KOKAI) Publication No. 8-54331 is a technique in which the above-mentioned disadvantages in the technology are overcome. That is to say, in this technique, the fatigue test can also be performed on ultrathin plates and a quick fatigue test is realized with application of the resonance. However, in the technique, reliable fatigue tests cannot be performed since control of amplitude is difficult due to energy absorption by resonance in which a part of the energy generated by a vibration source is absorbed in the test piece. In particular, it is more difficult to resonate the test piece reliably when the frequency is high and the amplitude is low. Therefore, the reliability is extremely reduced in the case in which a fatigue test at high frequency is performed.

SUMMARY OF THE INVENTION

An object of the present invention is to provide a fatigue test device for a thin plate in which the fatigue test can be reliably performed, and to provide a fatigue test method for the same.

The present invention provides a fatigue test device comprising a rod having ends in a longitudinal direction thereof, a vibration source for excitating the longitudinal end of the rod in the longitudinal direction thereof so as to form a standing wave having node portions and antinode portions formed therebetween, and a mounting means for mounting a test piece having a longitudinal direction at one of the antinode portions, the test piece being positioned such that the longitudinal direction thereof is perpendicular to the longitudinal direction of the rod.

The device having the above-described structure can make the test piece resonate, the test piece being secured such that the longitudinal direction thereof is perpendicular to the longitudinal direction of the rod in antinode portions of a standing wave generated by the excitation of the rod by exiting a longitudinal end of the rod by the vibration source. In this device, when a standing wave is generated in the rod by driving the vibration source, the amplitude of the standing wave can be easily controlled by the vibration source. Therefore, the amplitude of the antinode portion, at which the test piece is mounted, of the standing wave of the rod, can be controlled. For this reason, even if a part of energy is absorbed in the test piece, a reliable amplitude can be obtained, since this absorbed energy is smaller than the energy accumulated as a standing wave of the rod. Therefore, according to the invention, fatigue tests for thin plates which are excellent in reliability can be obtained.

In the present invention, the test piece is preferably mounted at the antinode portion except for the free end of the rod. When the standing wave is generated in the rod, the shape of the free end of the rod must be formed in a flat surface in order to generate reflected waves at the free end. In one case, the test piece must be supported at an edge of the rod in order to position the test piece at the antinode portions of the standing wave of the rod. Therefore, it is considered that the mounting means should be made to be adhesive. However, in actual tests, operations for mounting and removing the test piece with respect to the rod are difficult, and the adhesion surface may exfoliate in the fatigue test. It is desirable that the test piece be mounted at the antinode portions except for the free end of the rod in order to avoid such problems. For example, it is considered that the rod is divided into parts in the longitudinal direction thereof, and the parts hold the test piece.

In addition, it is desirable to have a measuring device for measuring displacement of the free end of the test piece and displacement of the free end of the rod so as to calculate amplitude stress given in the test piece. According to such an embodiment, the displacement of the free end of the rod is assumed to be the displacement of the excitation end of the test piece, and the displacement of the free end of the rod and displacement of the free end of the test piece are subtracted from each other, whereby bending deflection given to the test piece is calculated, thereby easily calculating amplitude stress given in the test piece.

As mentioned in the above, the present invention relates to a fatigue test device and also relates to a fatigue test method with the above-mentioned features. That is to say, a fatigue test method of the present invention comprises securing a test piece at an antinode portion of a standing wave generated by excitation of a rod having both ends in a longitudinal direction thereof such that a longitudinal direction of the test piece is perpendicular to the longitudinal direction of the rod and excitating the longitudinal end of the rod in the longitudinal direction thereof so as to resonate the test piece.

DETAILED DESCRIPTION OF THE PREFERRED EMBODIMENTS

In the following, forms of examples of the present invention are explained according to the figures.

Figure 1:
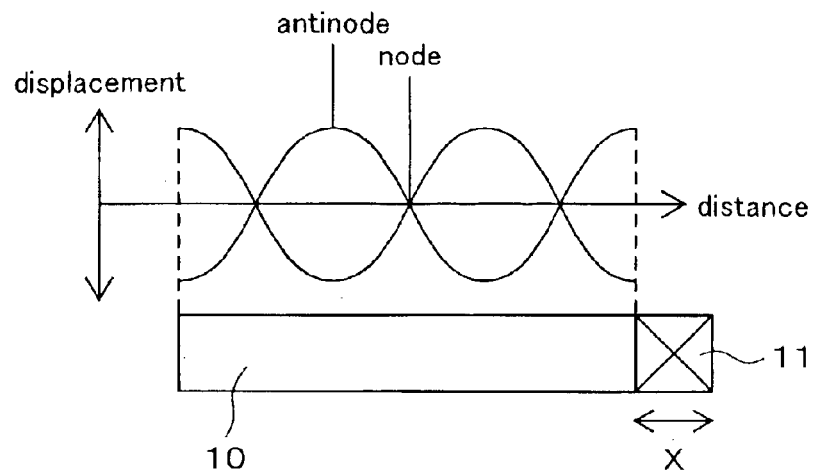
FIG. 1 shows an example of a device of the present invention and a condition of a standing wave generated in the rod.

A device such as is shown in FIG. 1 is proposed as a device in which excitation can be performed with reliable amplitude even if energy is absorbed in a test piece.

Figure 2:
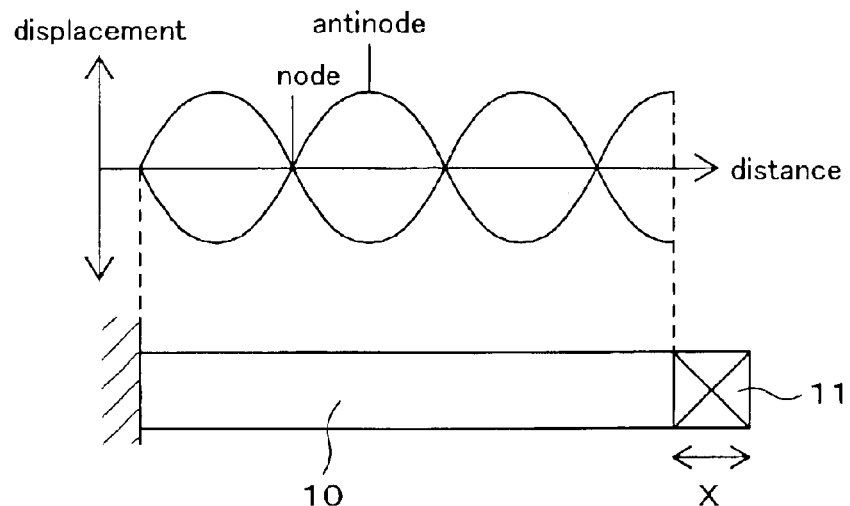
FIG. 2 shows another example of a device of the present invention and another condition of a standing wave generated in the rod.

As shown in this figure, vibration source 11 which excitates a rod 10 in axial direction X is disposed at an end of the rod 10. In this figure, a mounting means for mounting the test piece such that the longitudinal direction thereof is perpendicular to the longitudinal direction of the rod is not shown. It is simple for the structure of the device to make an end at the opposite side of rod 10 to be a free end. However, it is also possible to make the end to be a secured end as shown in FIG. 2. The standing wave which vibrates in axial direction X is generated in rod 10 by operating vibration source 11 at a resonant frequency of rod 10. In this case, although antinode portions of the standing wave strongly vibrate in the axial direction X of rods 10, node portions are not shown. The amplitude of this standing wave is easily controllable by vibration sources 11. Thus, the displacement of antinode portions of the standing wave can be easily controlled.

A test piece of flat plate is placed at antinode portions of the standing wave in this rod 10, such that the longitudinal direction thereof is perpendicular to the longitudinal direction of rod 10. The test piece is formed to have a shape and dimensions in which the test piece resonates at frequency of the standing wave generated in rod 10. By doing so, even if a part of the energy is absorbed in the test piece, reliable amplitude can be given to the test piece, since this absorption energy is less than energy accumulated as standing wave of rod 10.

Figure 3:
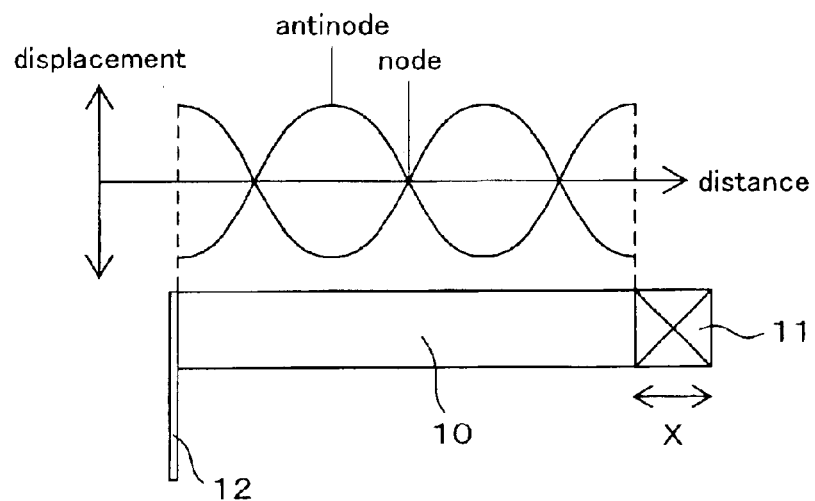
FIG. 3 shows an example in which a test piece is mounted in a device of the present invention and a condition of a standing wave generated in the rod.

As the simplest embodiment for a test piece in such a device, an embodiment in which the test piece 12 is mounted in the free end of rod 10 as shown in FIG. 3 may be mentioned. However, in order to produce a standing wave in the rod 10, the free end must be a flat surface so as to produce reflected waves at the free end. Therefore, it is necessary to support the test piece 12 at the edge of rod 10 in order to dispose test piece 12 at antinode portions of standing wave. Therefore, rod 10 and test piece 12 must be secured by a technique such as adhesion, and in actual tests, operations for mounting and removing the test piece 12 with respect to the rod are difficult, and the adhesion surface may exfoliate in the fatigue test.

Figure 4:
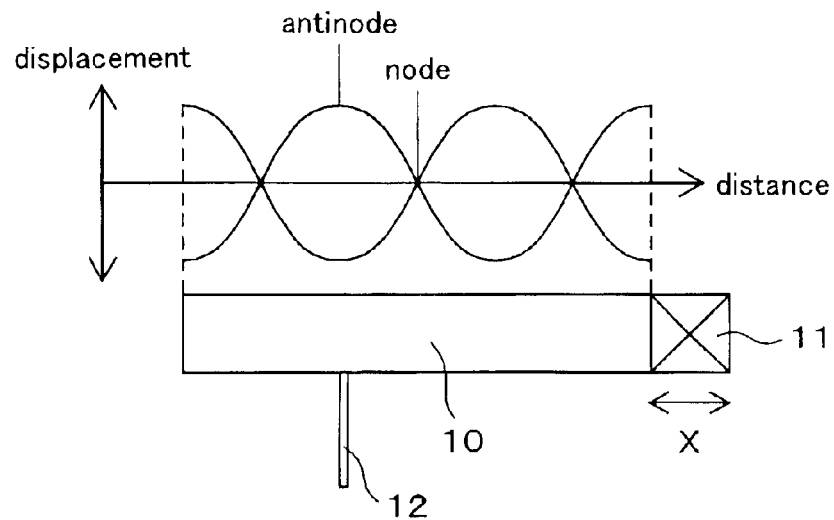
FIG. 4 shows another example in which a test piece is mounted in a device of the present invention and another condition of a standing wave generated in the rod.
Figure 5:
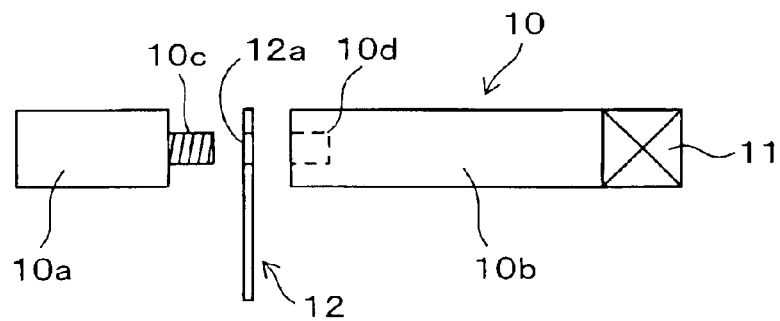
FIG. 5 is an exploded view of the rod, vibration source and test piece shown in FIG. 4.
Figure 6:
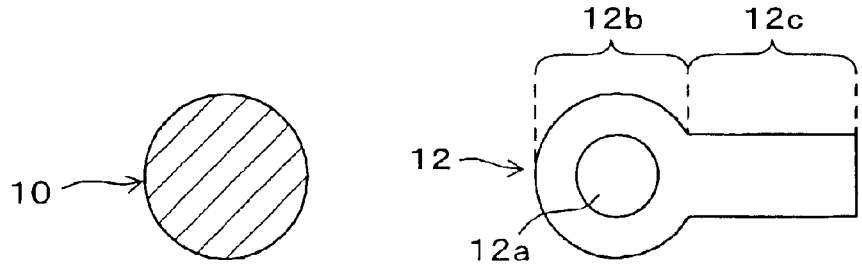
FIG. 6 is a cross-section showing a holding portion of the rod and a cross section showing the test piece.

Therefore, it is possible to avoid the above-mentioned problem by disposing test piece 12 in an antinode portion except for the free end of rod 10 as shown in FIG. 4. For example, as shown in FIG. 5, rod 10 is longitudinally divided from each other into rod part 10a and rod part 10b, and the test piece 12 is held by these parts. The test piece can be easily mounted or removed by providing an male screw portion 10c in rod part 10a and providing a female screw portion 10d in rod part 10b, and by providing mounting hole 12a in test piece 12 to form a mounting means, as shown in FIG. 4, In this case, as shown in FIG. 6, when rod 10 has a holding portion of which the cross-section is identical to a cross-section of test piece 12 which is held by rod 10, a standing wave can be more reliably generated in the test piece. Therefore, the fatigue test can be progressively reliably performed. Reference numeral 12c in FIG. 6 indicates a test portion of test piece 12.

Figure 7:
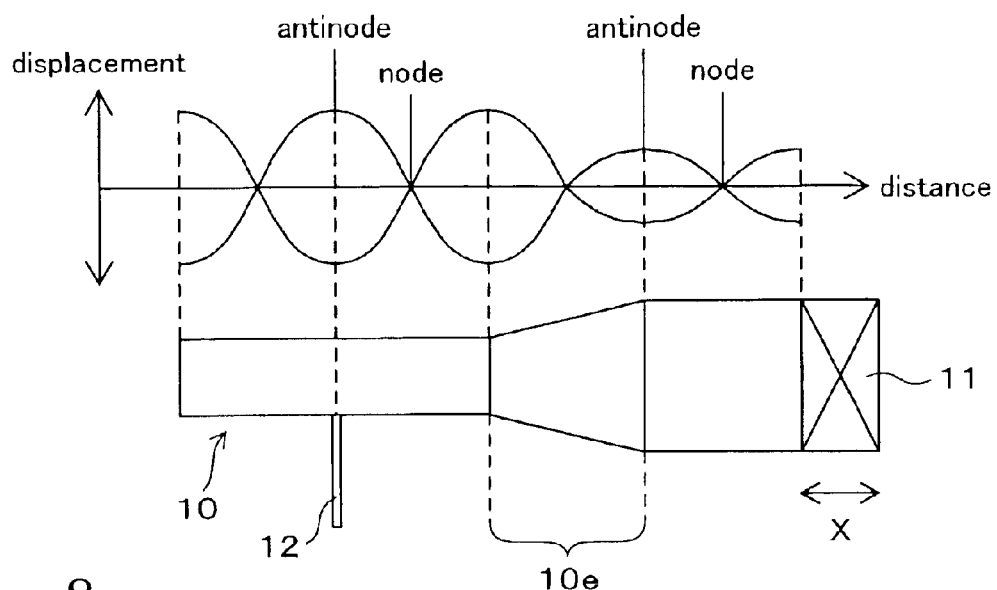
FIG. 7 shows another example in which a test piece is mounted in a device of the present invention and another condition of a standing wave generated in the rod.

Although the bending fatigue test for a thin plate can be performed by the above-mentioned method, vibration frequency must be increased in the case of performing fatigue at higher cycles in a short time. However, the output of the vibration source is constant, the amplitude is low when the vibration frequency is high, and so the fatigue test is difficult. In contrast, when the output of the vibration source is increased, the resonant frequency of vibration source is reduced. In order to overcome such problems, it is effective to provide horn 10e having a conical trapezoidal shape between the mounting position of vibration source 11 of rod 10 and the mounting position of test piece 12 of rod 10 as shown in FIG. 7. By increasing the amplitude of the standing wave by such a horn 10e, displacement of large amplitude can be obtained even if the frequency is high, whereby the fatigue test at high frequency can be realized.

Figure 8:
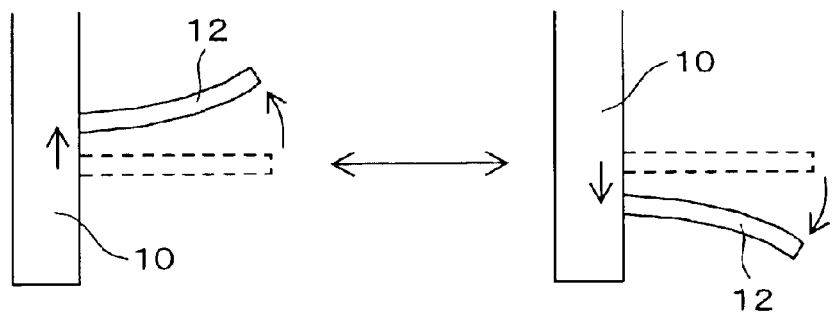
FIG. 8 shows an example of a vibration pattern of the test piece.
Figure 9:
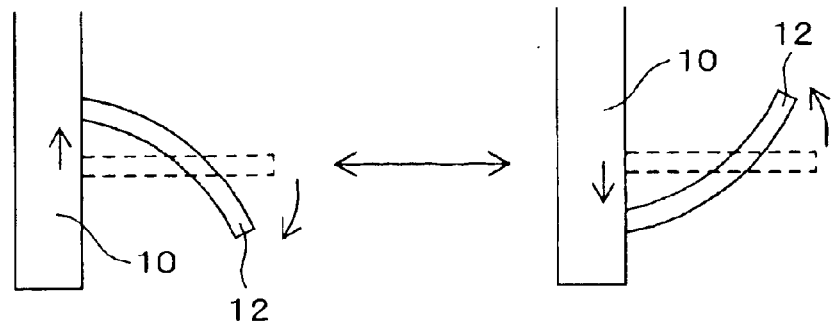
FIG. 9 shows another example of the vibration pattern of the test piece.
Figure 10:
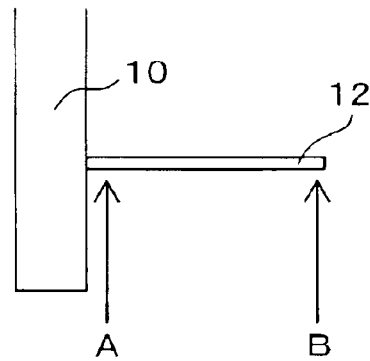
FIG. 10 shows an excitation end and a free end of the test piece in which the vibration pattern and amplitude of a test piece are measured.
Figure 11:
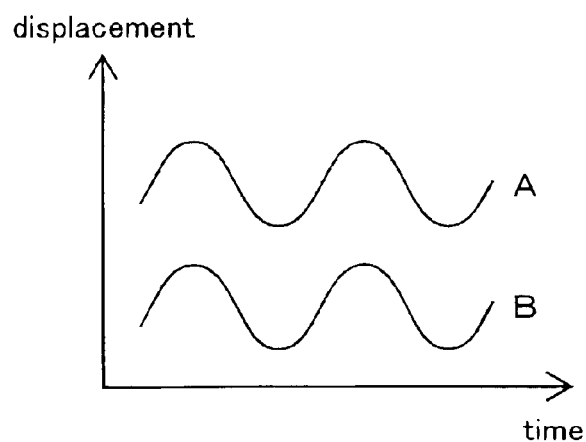
FIG. 11 shows an example of a waveform in an excitation end and a free end of the test piece.
Figure 12:
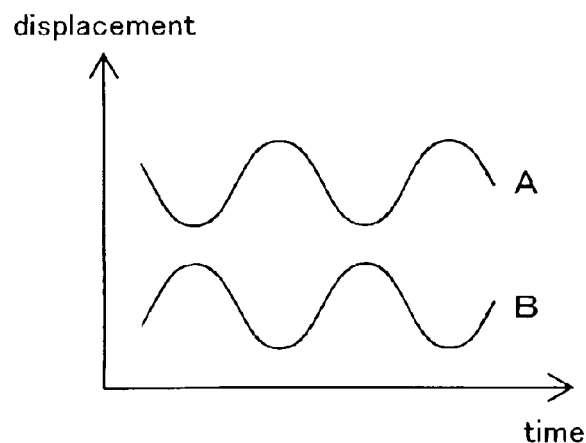
FIG. 12 shows another example of a waveform in the excitation end and the free end of the test piece.

By the above-mentioned composition of the fatigue test device, fatigue test of ultrathin plates can be performed. However, the actual load given to the test piece must be calculated, since the load parameter in the fatigue test is excitation displacement. Furthermore, although the test piece resonates, the form of the vibration changes according to delicate conditions, so that these conditions must be confirmed. FIG. 8 and FIG. 9 show typical examples of vibration patterns of the test piece 12 which is mounted at the rod 10. In order to measure such vibration patterns and amplitudes of test piece 12, it is necessary to measure aging variation in displacement of excitation end A of test piece 12 and displacement of free end B of the same, as shown in FIG. 10. This measurement results are waveforms of the coordinate phase shown in FIG. 11 in the case of FIG. 8, and waveforms of the opposite phase shown in FIG. 12 in the case of FIG. 9. Actually, amplitude stress is calculated by subtracting the displacement of excitation end A of test piece 12 and the displacement of free end B of test piece 12 from each other, to calculate bending deflection given to the test piece.

Figure 13:
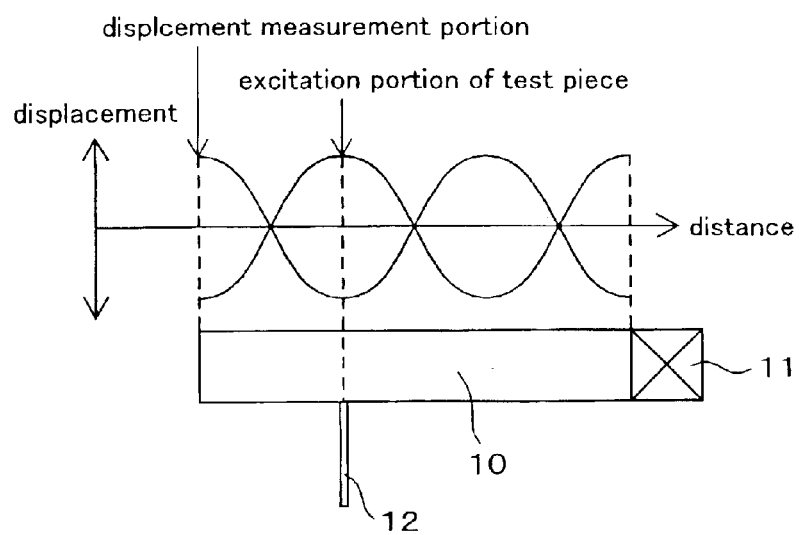
FIG. 13 shows another example in which a test piece is mounted in a device of the present invention and another condition of a standing wave generated in the rod.

It is difficult to measure displacement of excitation end A when test piece 12 is disposed at the antinode portion except for the free end of rod 10. However, since the amplitudes of the standing wave generated in the rod 10 are constant at each antinode portion, the amplitude measured at the free end of the rod 10 is used as the displacement which is input in the test piece. Therefore, as shown in FIG. 13, it is possible to easily judge the displacement of excitation end A of test piece 12 by measuring the displacement in the free end of rod 10. However, it should be noted that the standing wave in excitation end A of test piece 12 and the free end of rod 10 may be of opposite phase.

EXAMPLES

Next, an example of actually performing a fatigue test using the above-mentioned device is described.

Figure 14:
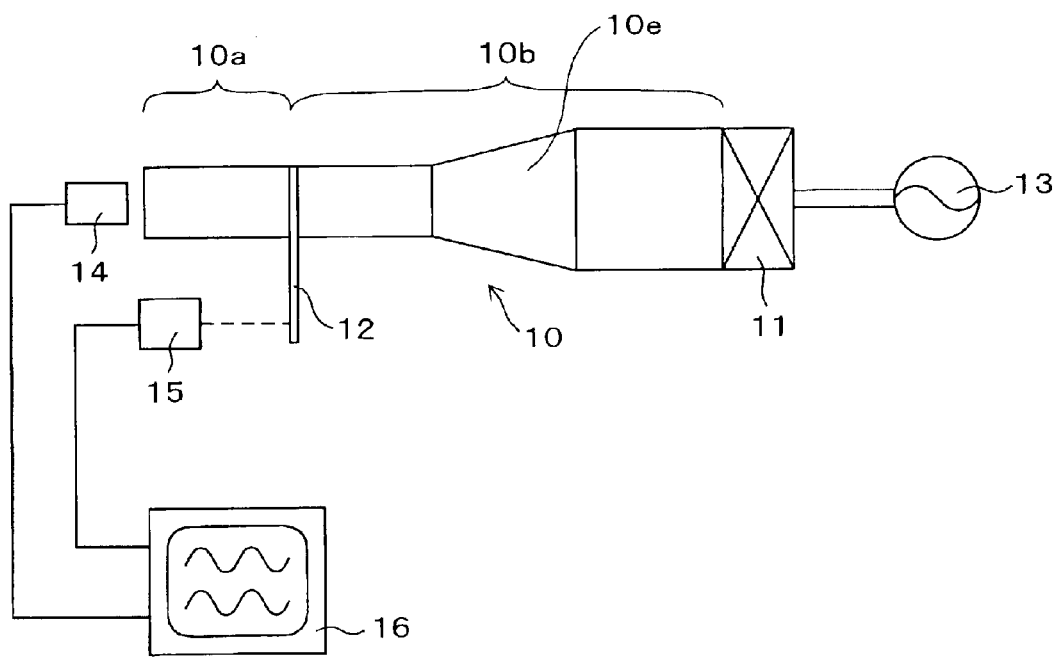
FIG. 14 is a block diagram showing a practical example.
Figure 15:
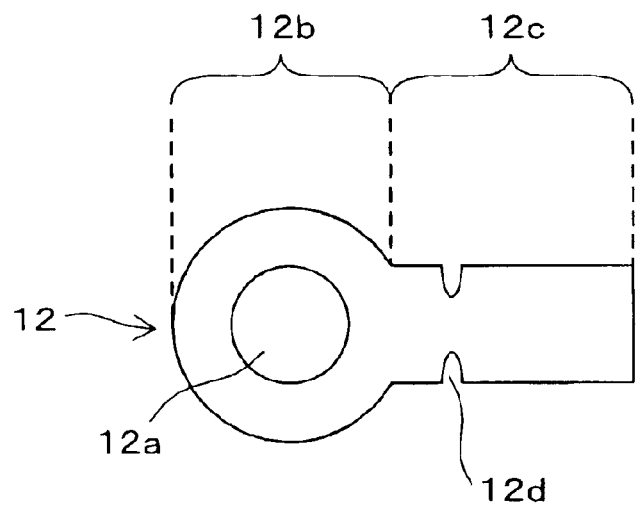
FIG. 15 is a sectional view of a test piece used in the practical example.

A block diagram of a practical example is given in FIG. 14. Reference numeral 11 in FIG. 14 shows a piezoelectric actuator as a vibration source, reference numeral 13 in this figure shows an oscillator, reference numeral 14 in this figure shows a vortex style of displacement gage, reference numeral 15 in this figure shows a laser displacement gage and reference numeral 16 in this figure shows an oscillator. Excitation frequency was 20 kHz, and shape and dimensions of test piece 12 and rod 10 were designed to resonate at 20 kHz. In such conditions, as shown in FIG. 15, a fatigue test was performed for test piece 12 made of a stainless steel (SUS304). Thickness of the test piece was 0.2 mm, and notch 12d was formed at a test portion 12c. Amplitude stress given in test piece 12 was calculated as a stress which was generated in the case of supplying relative displacement between excitation end A and free end B of test piece 12 to a cantilever beam.

Figure 16:
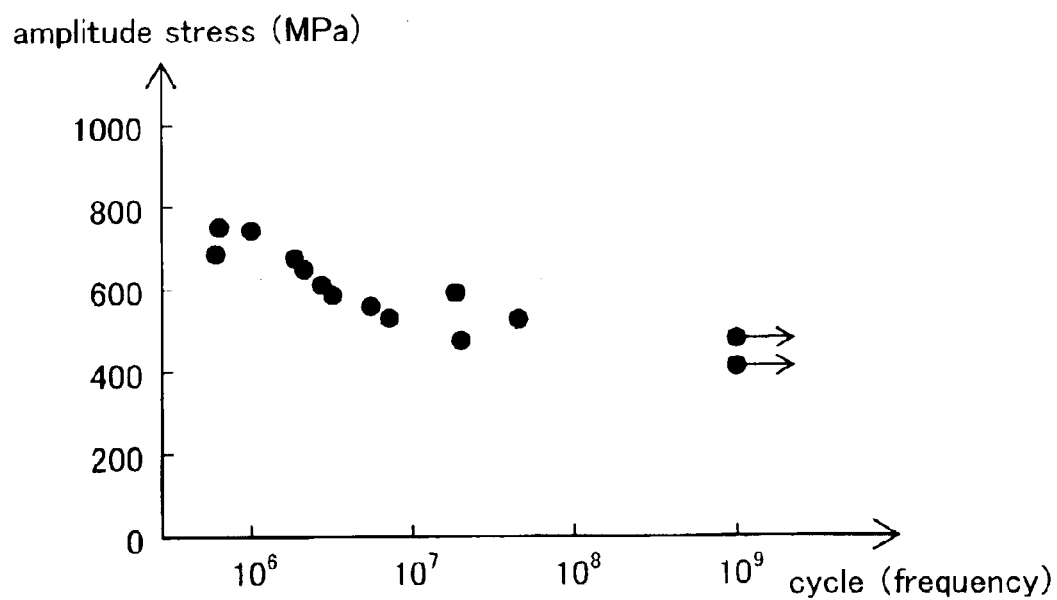
FIG. 16 shows the relationship between amplitude stress in the test piece and cycle.

S-N chart (relationship between amplitude stress and cycle given in the test piece) obtained as a result of the test is shown in FIG. 16. As shown in FIG. 16, the fatigue test using the ultrathin plates at high frequency could be performed with small dispersion, that is to say, with reliability. The fatigue test could also be performed quickly, since it was confirmed that the fatigue test up to $10^8$ cycles was completed in about 1.4 hours and the fatigue test up to $10^9$ cycles was completed in about 14 hours in the case of a test frequency of 20 kHz used in the practical example.

What is claimed is:

1. A fatigue test device comprising:
   a rod having ends in a longitudinal direction thereof;
   a vibration source for exciting at least one longitudinal end of the rod in the longitudinal direction thereof so as to form a standing wave having node portions and antinode portions formed therebetween;
   a mounting means for mounting one end of a test piece leaving a free end, the test piece having a longitudinal direction at one of the antinode portions and being positioned such that the longitudinal direction thereof is perpendicular to the longitudinal direction of the rod; and
   a measuring device for measuring displacement of the free end of the test piece so as to calculate amplitude stress imparted to the test piece.

2. A fatigue test device according to claim 1, further comprising a measuring device for measuring displacement of the free end of the rod.

3. A fatigue test method comprising:
   securing a test piece at an antinode portion of a standing wave generated by excitation of a rod having ends in a longitudinal direction thereof such that a longitudinal direction of the test piece is perpendicular to the longitudinal direction of the rod, with one end of the test piece mounted to the rod and an end opposite the mounted end of the test piece being a free end;
   exciting the longitudinal end of the rod in the longitudinal direction thereof so that the test piece resonates; and
   measuring displacement of the free end of the test piece to calculate amplitude stress given in the test piece.

4. A fatigue test method according to claim 3, wherein the test piece is mounted at at least one antinode portions except at the free end of the rod.

5. A fatigue test method according to claim 4, wherein the rod is divided into parts in the longitudinal direction thereof, and the parts hold the test piece.

6. A fatigue test method according to claim 5, wherein the rod has a holding portion of which the cross-section is identical to a cross-section of the test piece which is held by the rod.

7. A fatigue test method according to claim 3, wherein displacement of the free end of the test piece and displacement of the free end of the rod are measured to calculate amplitude stress given in the test piece.

* * * * *